United States Patent [19]
Lane

[11] Patent Number: 6,066,143
[45] Date of Patent: May 23, 2000

[54] PIN PULLER

[75] Inventor: Richard A. Lane, Fort Wayne, Ind.

[73] Assignee: Bristol-Myers Squibb Company, New York, N.Y.

[21] Appl. No.: 09/189,752

[22] Filed: Nov. 10, 1998

[51] Int. Cl.[7] .................................................. A61B 17/58
[52] U.S. Cl. .............................. 606/104; 606/72; 606/96; 606/205
[58] Field of Search .................... 606/65, 72, 73, 606/104, 205, 208, 144, 145, 147, 96

[56] References Cited

U.S. PATENT DOCUMENTS

| | | | |
|---|---|---|---|
| 1,659,112 | 2/1928 | Littlejohn | 606/147 |
| 1,918,889 | 7/1933 | Bacon | 606/147 |
| 5,300,082 | 4/1994 | Sharpe et al. | 606/208 |
| 5,376,096 | 12/1994 | Foster | 606/147 |
| 5,454,819 | 10/1995 | Knopfler | 606/147 |

OTHER PUBLICATIONS

"Articulating Surfaces Can Be Inserted or Removed Easily During Surgery" 1987 Zimmer Brochure.
Knee Systems Insall/Burstein II Modular Knee System, p. A217 1993 Zimmer Product Catalog.
Knee Systems Insall/Burstein II Modular Knee System, p. A222 1993 Zimmer Product Catalog.

*Primary Examiner*—Michael Buiz
*Assistant Examiner*—Daphna Shai
*Attorney, Agent, or Firm*—Cary R. Reeves

[57] ABSTRACT

A pin puller has a receiving end which holds the head of a pin securely and a mechanism for multiplying a handle squeezing force. The squeezing force is redirected to axially pull the pin from a bone.

9 Claims, 3 Drawing Sheets

PIN PULLER

BACKGROUND OF THE INVENTION

The present invention relates to surgical instruments used to remove temporary fixation pins as used in orthopaedic surgery to connect instruments to bone. In particular the device is designed to remove headed pins.

Orthopedic surgery requires the use of template, measuring, cutting, and other devices temporarily affixed to the bones. These devices can be affixed using a variety of methods, one of which is the use of pins with heads. Once the surgeon is finished with the device, the pins must be removed. The pins, which are driven in a manner similar to nails, are firmly held in the bone. Pins should be removed using a force applied parallel to the longitudinal axis of the pin. Removing the pins using a claw hammer type of remover would damage the pins, the device, and the underlying bone. Equipping the pins with heads offers a gripping surface to aid in pin removal. Prior art pin removers are like pliers, gripping the head of the pin in the jaws while force is applied to the jaws by the handles of the pin puller. The prior art pin pullers require the user to pull the pin out using the strength of the user. Often, when the frictional force is overcome, the pin moves quite freely, allowing the user's hand and arm to move in an uncontrolled manner. The user's hand and arm can strike an inanimate object or a bystander, potentially injuring both. Prior art pin pullers also do not securely capture the pin during removal. The pin is often dropped after removal, requiring resterilization of the pin and delay of the surgery.

SUMMARY OF THE INVENTION

The present invention solves the problems of the prior art by providing a pin puller with a receiving end which holds the head of the pin securely during removal and a mechanism for multiplying the force that the user can apply and applying the force parallel to the long axis of the pin. The receiving end can be a slip fit or a snap fit around the head of the pin. The force multiplying mechanism can be a system of levers or inclined planes.

Accordingly it is an object of the invention to provide a pin puller with a receiving end to securely hold the head of a pin during removal.

Another object of the invention is to provide a pin puller with a mechanism for multiplying the users force to smoothly pull the pin from the bone.

Other objects of the invention will become apparent upon a reading of the following description taken with the accompanying drawings.

DETAILED DESCRIPTION OF THE INVENTION

Figure 1:
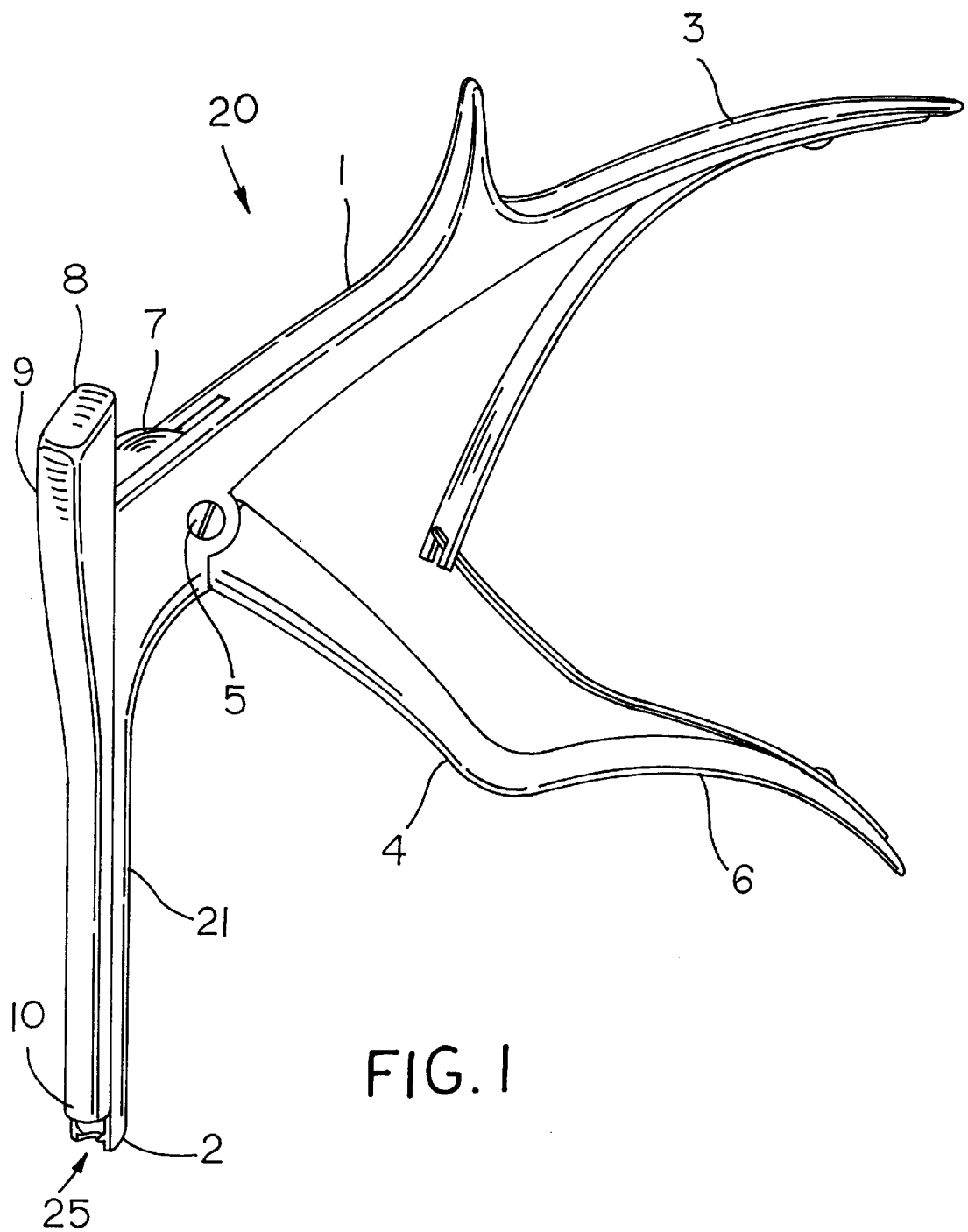
FIG. 1 is a perspective view of the pin puller.

The following description of the preferred embodiment is not intended to be exhaustive or to limit the invention to the precise form disclosed. Rather it is chosen in order to explain the invention so that one skilled in the art might utilize its teachings.

FIGS. 1–4 depict the preferred embodiment of the pin puller of the present invention. The pin puller 20 is comprised of three members: a stationary member 1, a pivoting member 4, and a sliding member 9. Stationary member 1 is generally L-shaped and includes a receiving end 2 which is shaped to engage a head 22 of a headed pin 23. Stationary member 1 also includes a support portion 21 and a handle end 3 which forms one half of a hand grip. The pin head 22 and receiving end 2 have complimentary shapes to provide positive engagement for axial pulling. For example, the pin head 22 can be a cylindrical solid with a groove 24 and the receiving end 2 can form a channel 25 with a raised rib or tongue 26 as shown in the preferred embodiment. Pivoting member 4 is pivotally attached at its pivot end 7 to the stationary member by a screw 5 forming a pivot point. A portion 6 of the pivoting member forms the other half or the handle as shown. The sliding member 9 is mounted for sliding on the support member 21 and has a first end 8 and a second end 10. Pivot end 7 of the pivoting member engages the first end 8 of sliding member 9 such as by pressing against a pin or the end of a slot in the underside of the sliding member (not shown) as is known in the art for bone punches and elongated forceps. When the portion 6 is moved toward the handle end 3 by pivoting around the screw 5, the sliding member 9 is pushed forward along the support portion 21 of the stationary member 1. The second end 10 of the sliding member 10 is thus moved forward past the receiving end 2.

Figure 2:
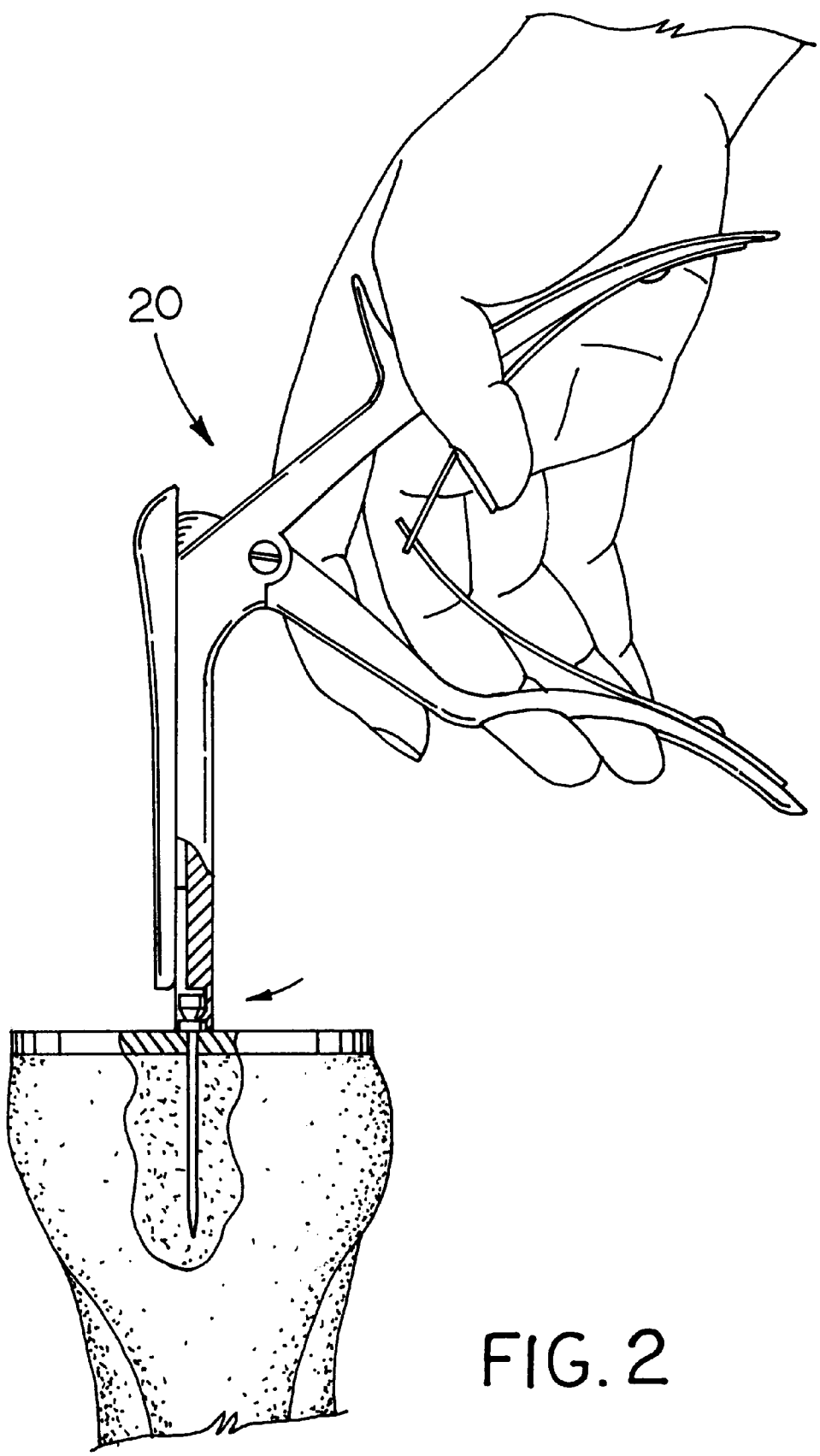
FIG. 2 is a partial cross sectional view of the pin puller in use removing a headed pin from a tibial instrument and tibial bone.
Figures 3, 4:
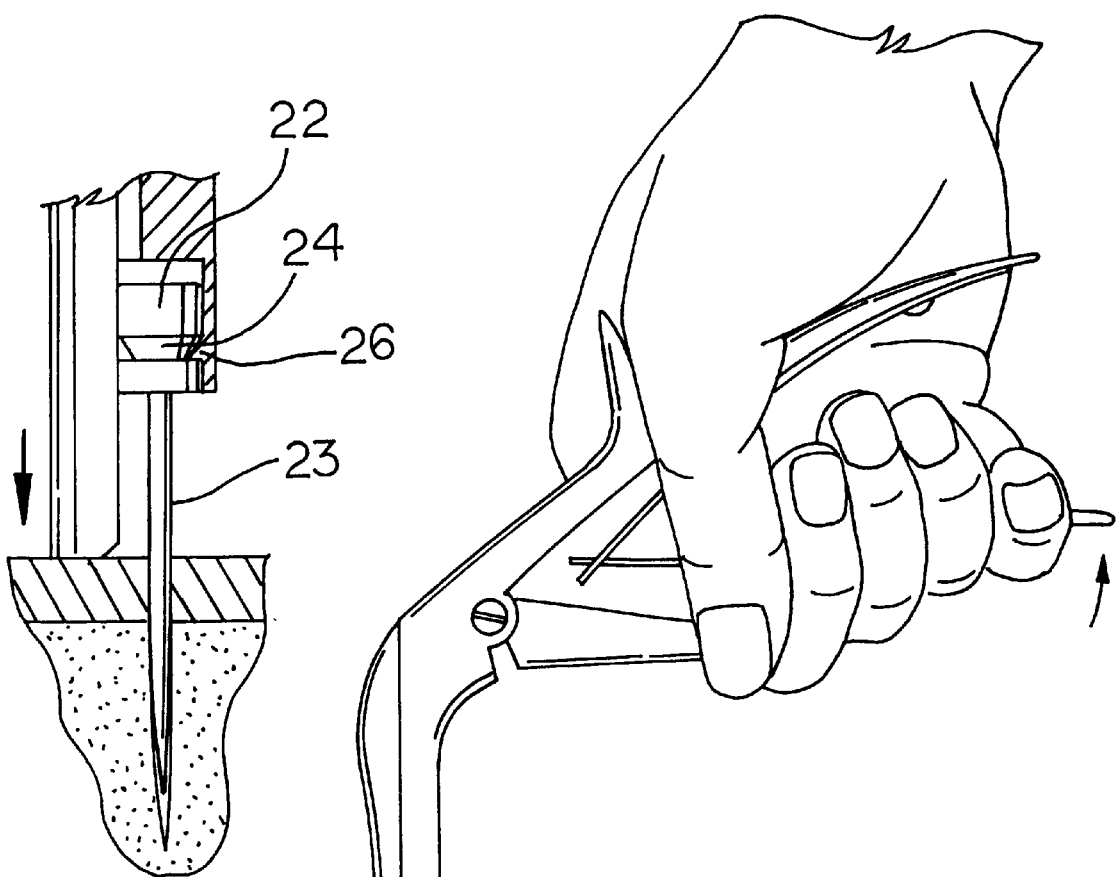
FIG. 3 is a partial cross sectional view of FIG. 2 with the pin shown being removed.
FIG. 4 is an enlarged view of the circled area of FIG. 3 identified by numeral 30.

In use, the receiving end 2 is brought into engagement with a pin head 22 as shown in FIG. 2. The channel 25 fits around a portion of the head 22 with the rib 26 engaging the groove 24. The pivoting member 4 is then squeezed toward the handle end 3 causing the pivot end 7 to move forward. Pivot end 7 presses against the first end 8 driving sliding member 9 forward toward receiving end 2. With continued squeezing, the second end 10 of the sliding member passes the screw head 22 thereby trapping it in the channel 25. With still further squeezing, the second end 10 makes contact with the material surrounding the pin shaft. As shown in exemplary FIG. 2, the material surrounding the pin is a metal plate lying on top of the bone. As the second end pushes against the surrounding material and the first end 10 and the receiving end 2 continue to move apart, the pin is pulled from the bone.

The lever and pivot arrangement of stationary member 1 and pivoting member 4, with portion 6 being longer than pivot 7, creates a mechanical advantage such that a relatively small squeezing force results in a relatively large pin extraction force, or in other words, a relatively large squeezing distance produces a relatively small sliding distance of the engagement member with respect to the sliding member. The engagement of the pivoting member 4 with the sliding member 9 converts the pivoting motion of the handles into a linear sliding motion so the pin 23 is pulled axially, further easing the extraction and reducing damage to the pin.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An instrument for removing a pin from a bone, the pin being of the type inserted into a bone to mark a location on the bone or to attach another device to the bone, the pin having a shank with a longitudinal axis and an exposed end, there being a bearing region surrounding the inserted pin shank on the bone or other device against which a compressive force can be applied, the instrument comprising:

first and second handles;

an engagement member configured to firmly grip a said exposed end of a said pin in order to apply a force along a said pin longitudinal axis, the engagement member being connected to the first handle; and a sliding member mounted in relative sliding relationship to the engagement member and connected to the second handle such that squeezing of the handles toward one another causes the sliding member to slide relative to the engagement member and to contact a said region surrounding the pin shank whereby a said engagement member and pin are forced away from a said bone and a said pin is smoothly withdrawn from a said bone.

2. The instrument of claim 1 wherein the engagement member further includes an undercut opening for positively engaging a said exposed end of a said pin to lock a said pin and the engagement member together for longitudinal force transmission.

3. The instrument of claim 2 wherein the sliding member is movable between a first position in which the undercut opening is uncovered to permit a said exposed end of a said pin to be laterally inserted into and removed from the undercut opening and a second position in which the undercut opening is covered to prevent a said exposed end of a said pin from being laterally inserted into and removed from the undercut opening.

4. In combination, a pin and an instrument for removing the pin from a bone, the pin being of the type inserted into a bone to mark a location on the bone or to attach another device to the bone, the pin having a shank with a longitudinal axis and an exposed end, there being a bearing region surrounding the inserted pin shank on the bone or other device against which a compressive force can be applied, the improvement comprising:

first and second handles;

an engagement member configured to firmly grip the exposed end of the pin in order to apply a force along the pin longitudinal axis, the engagement member being connected to the first handle; and a sliding member mounted in relative sliding relationship to the engagement member and connected to the second handle such that squeezing of the handles toward one another causes the sliding member to slide relative to the engagement member and to contact the region surrounding the pin shank whereby the engagement member and pin are forced away from the bone and the pin is smoothly withdrawn from the bone.

5. The instrument of claim 4 wherein the pin further includes an enlarged head on the exposed end and the engagement member further includes an undercut opening for positively engaging enlarged head to lock the pin and the engagement member together for longitudinal force transmission.

6. The instrument of claim 5 wherein the sliding member is movable between a first position in which the undercut opening is uncovered to permit the head of the pin to be laterally inserted into and removed from the undercut opening and a second position in which the undercut opening is covered to prevent the head of the pin from being laterally inserted into and removed from the undercut opening.

7. An instrument for pulling a pin having an enlarged head and a shank from a bone, the instrument being generally of the type having a first member having a first handle and a first working end and a second member having a second handle and a second working end, the first and second members being joined at a pivot, the first and second handles being operable to cause relative sliding motion between the first and second working ends, the improvement comprising:

the first working end including an engagement portion configured to grip the pin for applying a force along the pin shank; and the second working end including a bearing portion such that squeezing of the handles toward one another causes the bearing portion to slide relative to the engagement portion and to contact the region surrounding the pin shank whereby the engagement portion and pin are forced away from the bone.

8. The instrument of claim 7 wherein the engagement portion includes an undercut opening for positively engaging the enlarged head of a pin to prevent axial separation of a pin and engagement portion.

9. The instrument of claim 8 wherein the second working end is movable between a first position in which the undercut opening is uncovered to permit the enlarged head of the pin to be laterally inserted into and removed from the undercut opening and a second position in which the undercut opening is covered to prevent the enlarged head of the pin from being laterally inserted into and removed from the undercut opening.

\* \* \* \* \*